(12) United States Patent
Sidhu

(10) Patent No.: US 12,263,054 B2
(45) Date of Patent: *Apr. 1, 2025

(54) SUCTION TOOL

(71) Applicant: SafeVac, LLC, Las Vegas, NV (US)

(72) Inventor: Jessy Sidhu, San Diego, CA (US)

(73) Assignee: SAFEVAC, LLC, Las Vegas, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/486,589

(22) Filed: Sep. 27, 2021

(65) Prior Publication Data

US 2022/0226087 A1    Jul. 21, 2022

Related U.S. Application Data

(63) Continuation of application No. 16/296,080, filed on Mar. 7, 2019, now Pat. No. 11,141,250.

(60) Provisional application No. 62/639,788, filed on Mar. 7, 2018.

(51) Int. Cl.
*A61C 17/08* (2006.01)
*A61C 17/06* (2006.01)
*A61M 1/00* (2006.01)

(52) U.S. Cl.
CPC ............ *A61C 17/065* (2019.05); *A61C 17/08* (2019.05); *A61M 1/79* (2021.05); *A61M 1/84* (2021.05)

(58) Field of Classification Search
CPC ....... A61C 17/04; A61C 17/043; A61C 17/08; A61C 17/092
See application file for complete search history.

(56) References Cited

U.S. PATENT DOCUMENTS

| | | | | |
|---|---|---|---|---|
| 2,637,106 A * | 5/1953 | Otis | ........................ | A61C 17/08 433/91 |
| 3,460,255 A * | 8/1969 | Hutson | ................... | A61C 17/08 433/91 |
| 3,864,831 A | 2/1975 | Drake | | |
| 4,883,426 A | 11/1989 | Ferrer | | |
| 7,335,023 B2 | 2/2008 | Mahlmann | | |
| 8,231,384 B2 * | 7/2012 | Sidhu | ..................... | A61C 17/08 433/92 |
| 8,393,898 B2 | 3/2013 | Mccary | | |
| 9,532,857 B2 | 1/2017 | Ronto | | |
| 10,390,916 B1 | 8/2019 | Rassibi | | |
| 11,141,250 B2 * | 10/2021 | Sidhu | ................... | A61C 17/065 |
| 2006/0110702 A1 * | 5/2006 | Mahlmann | ............ | A61C 17/08 433/96 |
| 2015/0196375 A1 | 7/2015 | Wegmann | | |

* cited by examiner

*Primary Examiner* — Ralph A Lewis
(74) *Attorney, Agent, or Firm* — Mintz, Levin, Cohn, Ferris, Glovsky and Popeo, P.C

(57) ABSTRACT

A suction tool for connection to a dental suction system can include an elongate body, a tip portion, and a screen mechanism positioned within the elongate body. The tip portion can extend over at least a portion of the elongate body. The tip portion can include an upper portion and a lower portion integrally formed with the upper portion and at least partially spaced apart from the upper portion by a recessed portion.

20 Claims, 8 Drawing Sheets

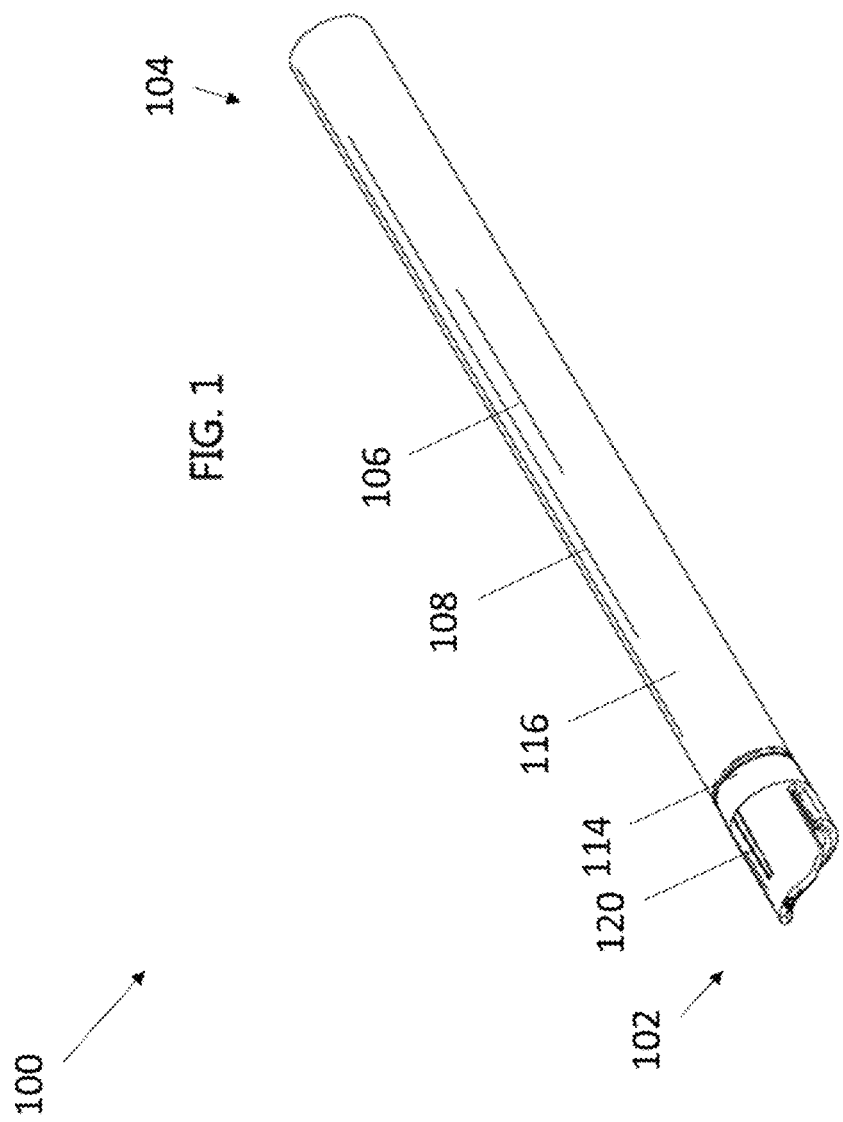

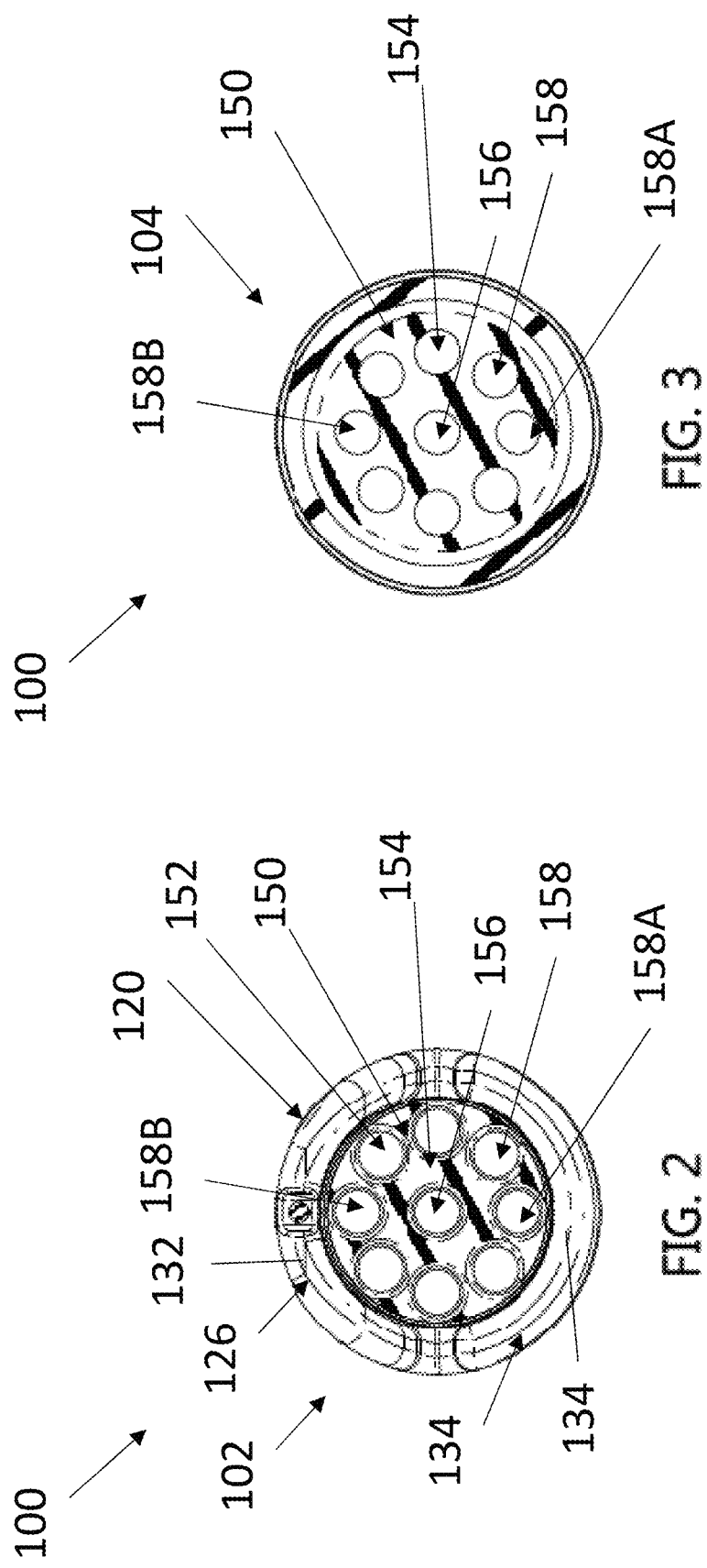

SUCTION TOOL

CROSS-REFERENCE TO RELATED APPLICATIONS

This application claims priority to U.S. Provisional Application No. 62/639,788, filed on Mar. 7, 2018, and titled "Suction Tool," the entirety of which is incorporated by reference herein.

BACKGROUND

The disclosure generally relates to tools for medical use, such as dental tools. More specifically, the disclosure relates to suction tools for use during dental procedures. Dental professionals often use suction devices to evacuate or remove saliva, other fluids, biological debris, dental material and other matter from the mouths of patients during various procedures. In procedures where a dental professional is required to evacuate matter from a patient's mouth, a high volume evacuator device may be used. Embodiments disclosed herein relate to HVE devices and methods for evacuating matter from a patient's mouth during a dental procedure.

SUMMARY

Aspects of the current subject matter relate to a suction tool for use in dental procedures, among other medical procedures.

According to some aspects, a suction tool for connection to a dental suction system is provided. The suction tool may include an elongate body, a tip portion, and a screen mechanism. The elongate body may include a first material. The elongate body may include a longitudinal axis extending between a connection end portion that is configured to connect to the dental suction system and a suction end portion, an inner surface defining a central passageway extending from the connection end portion to the suction end portion, and an outer surface. The tip portion may extend over at least a portion of the elongate body and be positioned at the suction end portion of the elongate body. The tip portion may include an upper portion, and a lower portion integrally formed with the upper portion and at least partially spaced apart from the upper portion by a recessed portion. The screen mechanism may be positioned within the central passageway. The screen mechanism may include a plurality of openings that are configured to allow evacuated matter to pass through.

In some aspects, the plurality of openings are circular. In some aspects, the plurality of openings include a central opening concentrically aligned with the elongate body, and a plurality of outer openings uniformly spaced and arranged in a shape that is concentrically aligned with the central opening.

In some aspects, the tip portion further includes an external surface that is approximately aligned with the outer surface of the elongate body to form a smooth transition between the external surface and the outer surface. In some aspects, the elongate body further includes an elongate region having a maximum diameter, and a transition region positioned between the elongate region and the tip portion. The transition region may have a maximum diameter that is greater than the maximum diameter of the elongate region. In some aspects, the transition region is tapered between the elongate region and the tip portion. In some aspects, the first material is different from the second material. In some aspects, the elongate body has a wall thickness extending between the inner surface and the outer surface. The wall thickness may define a unitary body that extends from the connection end portion to at least the tip portion.

According to some aspects, a method of reducing noise caused by suction through a dental suction tool may be provided. The method may include providing a dental suction tool. The suction tool may include an elongate body. The elongate body may include a first material and a central passageway extending from a connection end portion to a suction end portion. The elongate body may define a unitary body. The suction tool may include a tip portion extending over at least a portion of the elongate body and positioned at the suction end portion of the elongate body. The tip portion may include a second material, and a pressure prevention recess positioned between an upper portion and a lower portion.

In some aspects, the first material is the same as the second material. In some aspects, the first material is different from the second material. In some aspects, the second material comprises a rubber material.

In some aspects, the dental suction tool further includes a screen mechanism positioned within the central passageway. The screen mechanism may include a plurality of openings that are can allow evacuated matter to pass through.

According to some aspects, a method of reducing noise caused by suction through a dental suction tool is provided. The method may include providing a dental suction tool. The suction tool may include an elongate body including a first material and a central passageway extending from a connection end portion to a suction end portion. The connection end portion may have a proximal most end, and the suction end portion may have a distal most end. The suction tool may include a tip portion extending over at least a portion of the elongate body and positioned at the suction end portion of the elongate body. The tip portion may include a second material that is different from the first material. The suction tool may include a screen mechanism including a plurality of openings that are configured to allow evacuated matter to pass through. The screen mechanism may be positioned within the central passageway at a distance from the proximal most end that is less than 80% of a total length of the dental suction tool. The total length may extend from the proximal most end to the distal most end.

According to some aspects, a method of reducing noise caused by suction through a dental suction tool is provided. The method may include providing a dental suction tool. The suction tool may include an elongate body including a first material and a central passageway extending from a connection end portion to a suction end portion. The connection end portion may have a proximal most end, and the suction end portion may have a distal most end. The suction tool may include a tip portion extending over at least a portion of the elongate body and positioned at the suction end portion of the elongate body. The tip portion may include a second material that is different from the first material. The suction tool may include a screen mechanism including a plurality of openings that are configured to allow evacuated matter to pass through. The screen mechanism may be positioned within the central passageway at a distance from the distal most end that is greater than 20% of a total length of the dental suction tool. The total length may extend from the proximal most end to the distal most end.

According to some aspects, a method of reducing noise caused by suction through a dental suction tool may be provided. The method may include providing a dental suction tool. The suction tool may include an elongate body including a first material and a central passageway extending from a connection end portion to a suction end portion. The connection end portion may have a proximal most end and the suction end portion may have a distal most end. The suction tool may include a tip portion extending over at least a portion of the elongate body and positioned at the suction end portion of the elongate body. The tip portion may include a second material that is different from the first material. The suction tool may include a screen mechanism that includes a plurality of circular openings that are configured to allow evacuated matter to pass through. The plurality of circular openings may include a central opening concentrically aligned with the elongate body and a plurality of outer openings uniformly spaced and arranged in a shape that is concentrically aligned with the central opening.

According to some aspects, a method of manufacturing a suction tool is provided. The method may include forming an elongate body defining a unitary body. The elongate body may include a first material, a longitudinal axis extending between a connection end portion that is configured to connect to the dental suction system and a suction end portion, an inner surface defining a central passageway extending from the connection end portion to the suction end portion, and an outer surface. The elongate body may include a screen mechanism positioned within the central passageway. The screen mechanism may include a plurality of openings that are configured to allow evacuated matter to pass through. The method may include forming a tip portion extending over at least a portion of the elongate body and positioned at the suction end portion of the elongate body. The tip portion may include a second material different from the first material, an upper portion, and a lower portion integrally formed with the upper portion and at least partially spaced apart from the upper portion by a recessed portion.

According to some aspects, a method of performing a dental procedure comprises using a suction tool having one or more of the features of the suction tool described herein. The dental procedure described herein may include one or more of evacuating saliva, other biological matter, and/or non-biological matter, bonding, braces, bridges, implants, crowns, caps, extractions, dentures, filings, repairs, gum surgery, oral examinations/evaluations, root canals, sealants, teeth whitening, teeth and/or mouth cleaning, veneers, prophylaxis, periodontal services and maintenance, fluoride treatment, oral therapies, sealant applications, palliative treatment of dental pain, mouth debridement, restorations (e.g., amalgam restorations, resin restorations, etc.), and/or any other oral or dental procedure.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIG. 1 is a front, side, and top perspective view of an embodiment of a suction tool including a tip portion and a screen mechanism.

FIG. 2 is a front view of the suction tool of FIG. 1.

FIG. 3 is a rear view of the suction tool of FIG. 1.

DETAILED DESCRIPTION

Figure 4:
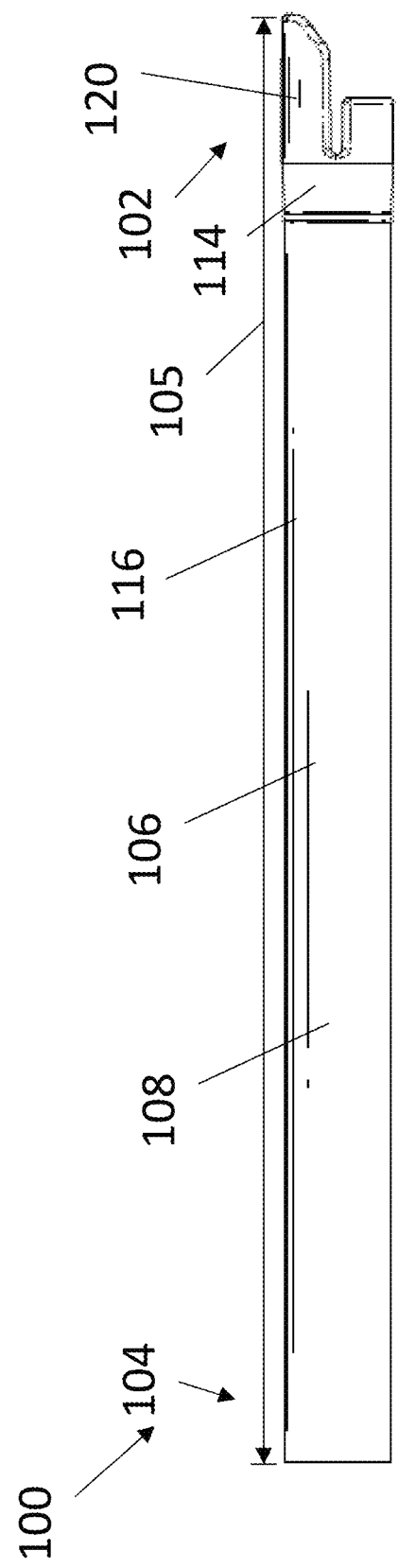
FIG. 4 is a side view of the suction tool of FIG. 1.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Suction tools can include high volume evacuator (HVE) devices and/or saliva ejector devices. HVE devices and saliva ejector devices can be coupled with a source of negative pressure, such as a vacuum or suction system. The source of negative pressure can assist in transferring matter from a first location to a second location. Generally, saliva ejector devices can remove excess saliva from a patient's mouth during a dental procedural. Typically, HVE devices can evacuate saliva and/or other matter from a patient's mouth during a dental procedure. For example, HVE devices can be used to evacuate saliva, other biological matter, and/or non-biological matter including, but not limited to, dental restorative materials and restorations. Accordingly, HVE devices may typically be formed from rigid materials and saliva ejector devices can typically be formed from more flexible materials. In certain arrangements, a central passageway in the HVE devices can typically be larger than the central passageway of the saliva ejector devices.

Inserting a typical HVE device into a patient's mouth can lead to inadvertent traumas, such as lacerations or hematomas in the patient's mouth. In many cases, the dental professional and/or patient may not notice these traumas when they occur because the patient's mouth has been anesthetized. Traumas caused by HVE devices can result in post-procedure discomfort for the patient and/or other complications, such as infections that are of the viral, bacterial, and/or fungal.

Certain materials including biological and/or non-biological materials that aid the dental professional during a procedure such as cotton rolls and/or gauze, can become lodged in the HVE device and/or suction system during a procedure. This can block the source of negative pressure or suction. Typically, to remedy such a blockage, the dental professional must stop working on the patient, turn the suction system off, disassemble or partially disassemble the HVE device and/or suction system, remove the blockage, reassemble the device, and turn the suction system back on, before resuming work on the dental procedure.

Moreover, in some situations, sterilized objects, for example, implants, grafts (e.g., tissue and/or bone, among others), and/or restorations, can inadvertently be evacuated through an HVE device and transported to an unsterile location, such as a filter, within the suction system. In such circumstances, the dental professional must spend a great deal of time re-sterilizing the evacuated object before the object can be placed into the patient's mouth. Because many dental professionals see patients in ten or fifteen minute increments, delays due to HVE device/system blockages and/or dental restoration (e.g., crowns, veneers, inlays, onlays, and/or implants, among others) retrievals can be costly to the dental professional and/or burdensome for the patient. In some cases, large objects that are evacuated with an HVE device can damage the suction system. Such damage can result in longer delays while the equipment is repaired in addition to substantial repair costs.

Typical HVE devices may create an unwanted high level of noise. Noise during dental procedures can be hazardous to the user, such as the physician, and/or to the patient. Any amount of exposure to noise, such as prolonged exposure to noise from the HVE devices can lead to some amount of noise-induced hearing loss or impairment for the dental professional and/or the patient. For example, dental professionals, including physicians or assistants, and/or patients can be exposed to high levels of noise over an extended period of time during a procedure up to or more than 4 hours, 5 hours, 6 hours, 7 hours, 8 hours, or 9 or more hours at a time. The noise-induced hearing loss can be permanent and/or can compound over time. In some situations, noise caused by HVE devices can lead to dental anxiety or fear in the patients. The noise from the HVE devices can cause discomfort and/or an annoyance to the patient or the dental professional, making the patient's experience less pleasant. As described below, embodiments of the suction tool disclosed herein can significantly reduce noise exposure to the dental professionals and/or patients. Such configurations can provide a safer working environment for dental professionals and a more comfortable and/or safer environment for dental procedures.

Embodiments disclosed herein generally relate to HVE devices that can evacuate saliva and other matter, for example, from a patient's mouth during a dental procedure. Some embodiments described herein related to HVE devices that can reduce the level of noise that is produced in use. Some embodiments disclosed herein relate to HVE devices that can include a tip portion that can help to reduce inadvertent traumas caused by the HVE device during a dental procedure. Additionally, various embodiments disclosed herein relate to HVE devices that can include a screen mechanism. The screen mechanism can help to limit blockages in HVE devices and/or suction systems. Certain embodiments relate to HVE devices that can include a collection region positioned between the screen mechanism and a suction portion to catch certain materials that are inadvertently evacuated with an HVE device and/or to prevent the materials from further evacuation through the un-sterile suction system. For example, typically the patient is in the supine position during a dental procedure. Placing implant parts and/or tools in the patient's mouth can be difficult, as the mouth becomes more crowded with certain tools and/or implant parts. It can be difficult for the dental professional to view and/or access certain regions of the patient's mouth. Dropped and/or misplaced dental implants, for example, can become problematic. Embodiments of the screen mechanism described herein can help to catch dental implants or other dental restorations and/or other materials to prevent the parts from being swallowed by the patient and/or being drawn into the suction system. For example, if a dental implant, or other dental restorations, among other materials falls into the patient's mouth, the suction system can suck the material into the suction tool. The screen mechanism can catch the material within a collection region of the suction tool. The material may be held against a surface of the screen mechanism due to the suction pressure caused by the suction system. Such configurations can help to save a significant amount of money, as dental replacement parts can be very expensive. Certain embodiments described herein can allow the dental implants or other materials to be simply dropped onto a tray from the collection region when the suction system is disabled.

Several non-limiting examples of embodiments will now be described with reference to the accompanying figures, wherein like numerals refer to like elements throughout. The terminology used in the description presented herein is not intended to be interpreted in any limited or restrictive manner, simply because it is being utilized in conjunction with a detailed description of certain specific embodiments. Furthermore, embodiments can include several novel features, no single one of which is solely responsible for its desirable attributes or which is essential to practicing the technology herein described.

FIGS. 1-8 illustrate an example of a suction tool 100. The suction tool 100 can be used for medical purposes among other purposes. For example, as mentioned above, the suction tool 100 can be used during dental procedures. The suction tool 100 can include a suction end portion 102 and a connection end portion 104. The suction end portion 102 can be positioned opposite the connection end portion 104. The connection end portion 104 can releasably attach to a source of negative pressure, such as a suction or vacuum system. The suction end portion 102 can be configured to be placed in the patient's mouth and can draw matter from the patient's mouth for evacuation when the connection end portion 104 is attached to the source of negative pressure.

The suction tool 100 can include a total length 105. The length 105 can extend between a distal most end of the suction end portion 102 and a proximal most end of the connection end portion 104. The length 105 can vary. For example, non-limiting ranges for the length dimension may be between about 3 and about 30 centimeters and/or between about 13 and 16 centimeters, among other ranges less than 3 centimeters, greater than 30 centimeters, and/or other ranges therebetween. In some embodiments, the length 105 of the suction tool 100 is approximately 14.5 centimeters.

The suction tool 100 can include an elongate body 106. The elongate body 106 can be generally tube shaped. The suction tool 100 can include an outer surface 108 and an inner surface 110. The inner surface 110 can define a central passageway 112 that extends through the elongate body 106 in a longitudinal direction. The elongate body 106 can have an exterior wall that has a thickness defined by the distance between the inner surface 110 and the outer surface 108. In some embodiments, the elongate body 106 defines a unitary body. The unitary body may not include an aperture or other perforation passing through a wall thickness of the elongate body between the central passageway 112 and the exterior of the suction tool 100. Such configurations can desirably enhance sound properties and limit excess noise produced by the suction tool 100 in use. Such configurations can maintain better structural integrity. Such configurations can increase the amount of matter that is directed from the suction end portion 102 to the connection end portion 104 of the suction tool 100. Such configurations can be easier to sterilize after use. Such configurations can allow tissue or other matter to be retracted more safely.

In some embodiments, the elongate body 106 can have a uniform or varied cross-sectional shape and/or wall thickness along at least a portion of the elongate body 106. In some embodiments, the elongate body 106 can have a uniform or varied width or radius along at least a portion of the elongate body 106. For example, the elongate body 106 can be generally cylindrical along at least a portion of the elongate body 106. In some embodiments, the elongate body 106 can include a tip portion 120, a transition region 114, and/or an elongate region 116. The transition region 114, the elongate region 116, and/or the tip portion 120 can be integrally formed. The elongate region 116 can have a generally uniform width and/or radius. In some embodiments, the transition region 114 has a width and/or diameter or maximum width and/or maximum diameter that is greater than the width and/or diameter or maximum width and/or maximum diameter of the elongate region 116. In some embodiments, the transition region 114 has a width and/or a diameter or maximum width and/or maximum diameter that is the same as the width and/or the diameter or maximum width and/or maximum diameter of the elongate region 116. In some embodiments, at least a portion of the transition region 114 can be tapered radially outwardly between the elongate region 116 and the tip portion 120. In some embodiments, the transition region 114 transitions smoothly between the elongate region 116 and the tip portion 120 as shown in at least FIG. 6 and FIG. 7.

In some embodiments, the central passageway 112 has a cross-section that is uniform along the elongate body 106. In some embodiments, the central passageway 112 has a cross-sectional shape that varies along at least a portion of the elongate body 106. The cross-section of the central passageway 112 can be generally polygonal-shaped. The cross-section of the central passageway 112 can be rectangular and/or generally curvilinear, such as round, oval, or circular. A cross-section of the elongate body 106 can be generally polygonal, such as rectangular, and/or generally curvilinear, such as round, oval or circular.

Figure 8:
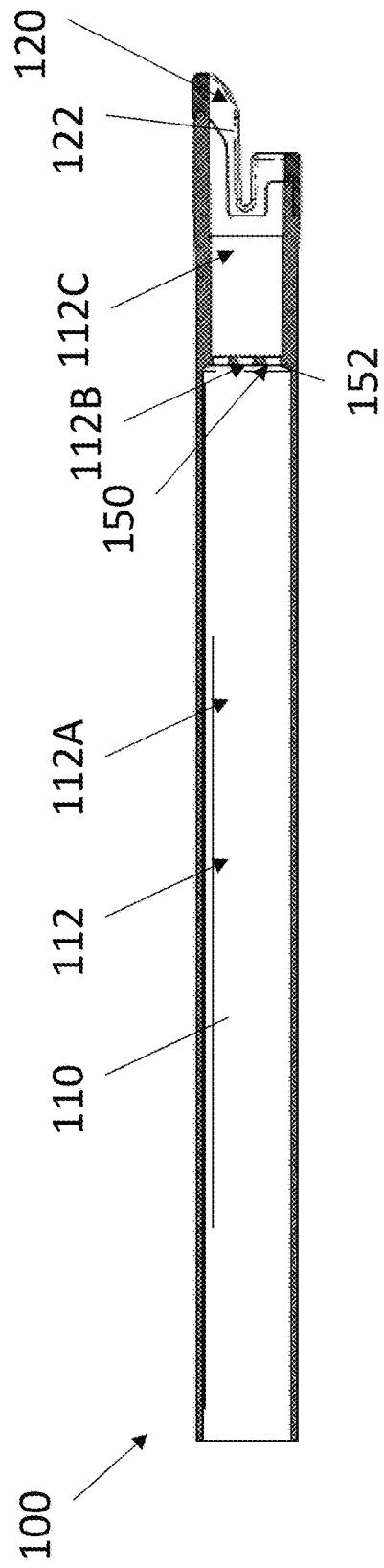
FIG. 8 is a side cross-sectional view of the suction tool of FIG. 1, taken along the line 8-8 as shown in FIG. 7.

As shown in at least the cross-sectional view of FIG. 8, the central passageway 112 can be defined by various portions. In some embodiments, the central passageway 112 can include an elongate passageway portion 112A, a screen passageway portion 112B, and/or a material collection passageway portion 112C, among other portions. The elongate passageway portion 112A can extend through at least a portion of the elongate region 116 of the elongate body 106. In some embodiments, the elongate passageway portion 112A can have a uniform width and/or radius. The elongate passageway portion 112A can align with a negative pressure source at the connection end portion 104.

The screen passageway portion 112B can extend through at least a portion of a screen mechanism 150, such as through one or more openings 152 in the screen mechanism 150, as explained in more detail below.

The material collection passageway portion 112C can extend from the screen passageway portion 112B to the suction end portion 102 of the suction tool 100. The material collection passageway portion 112C can receive matter from the patient's mouth or other regions. The material collection passageway portion 112C can be configured to collect and/or retain matter that does not pass through and/or beyond the screen mechanism 150. The material collection passageway portion 112C can have a width and/or diameter that is less that the width and/or diameter of the elongate passageway portion 112A. Such configurations can help to trap larger matter more easily. Such configurations can desirably help to reduce noise produced by the suction tool 100 in use. As mentioned above, typically the patient is in the supine position during a dental procedure. Placing implant parts and/or tools and/or dental restorations and/or other materials in the patient's mouth can be difficult, as the mouth becomes more crowded with certain tools and/or implant parts. It can be difficult for the dental professional to view and/or access certain regions of the patient's mouth. The reduced cross-sectional area at the tip portion 120 compared to at least a portion of the elongate body, such as the elongate passageway portion 112A can desirably help to create sufficient space for other instruments to be positioned within the patient's mouth.

In some configurations, the material collection passageway portion 112C has a uniform width and/or radius or a varied width and/or radius. In some embodiments, a portion of the material collection passageway portion 112C adjacent the suction end portion 102 has a larger width and/or radius than the portion of the material collection passageway portion 112C adjacent the screen mechanism 150. Such configurations can desirably help to trap matter within the material collection passageway portion 112C. In some configurations, the elongate body 106 includes an aperture between the central passageway 112 and the exterior of the suction tool 100.

In some embodiments, the wall thickness of the elongate body 106 is generally uniform. In some embodiments, at least a portion of the elongate body 106 has a varied wall thickness. As shown in the cross-sectional view of FIG. 8, the elongate body 106 can have varied wall thicknesses along the length of the suction tool 100. The wall thickness surrounding the elongate passageway portion 112A can be less than the wall thickness surrounding at least a portion of the material collection passageway portion 112C. Such configurations can desirably allow the suction end portion 102 of the suction tool 100 to be more rigid, have better stability, and/or better support to collect and/or retain more matter. Such configurations can desirably reduce material used to manufacture the suction tool 100. Such configurations can allow at least a portion of the elongate body 106, such as a portion surrounding the elongate passageway portion 112A to be rigid, yet somewhat flexible. Such configurations can desirably allow the dental professional to reach additional areas of the patient's mouth, while maintaining the structure of the suction tool 100. In some embodiments, a portion of the wall thickness surrounding the material collection passageway portion 112C adjacent the suction end portion 102 has a larger width than the portion of the wall thickness surrounding the material collection passageway portion 112C adjacent the screen mechanism 150. In some embodiments, the wall thickness increases along the transition region 114. Such configurations can create a funnel-like effect to direct the collected matter into the central passageway 112.

The elongate body 106 can be generally rigid. In some embodiments, the elongate body 106 can include generally rigid materials including, but not limited to, polymers, plastics, thermoplastics, composite materials (e.g., carbon fiber reinforced plastic), organic materials, cellulosic materials, rubbers, metals, and the like. For example, in some embodiments, the elongate body can include a United States Food and Drug Administration approved polypropylene that is not affected by bodily fluids and can be easily sterilized. In some embodiments, the elongate body 106 is somewhat or entirely flexible.

Figure 5A:
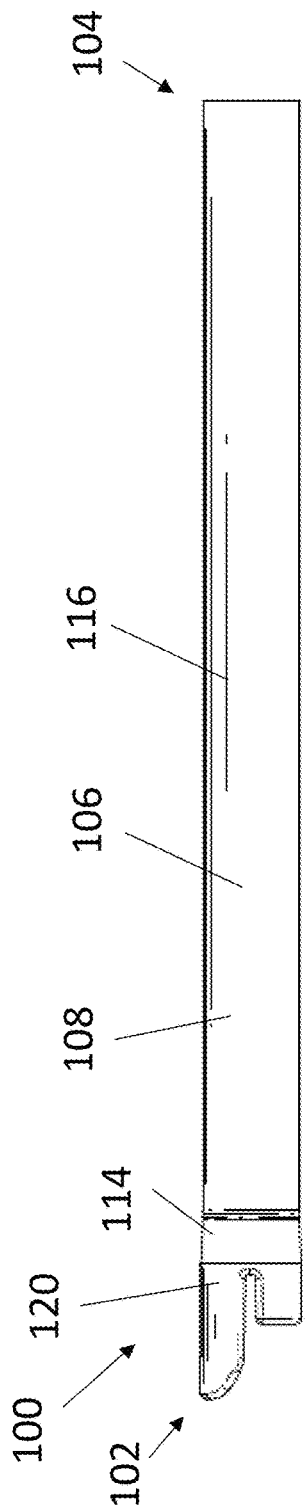
FIG. 5A is another side view of the suction tool of FIG. 1.
Figure 5B:
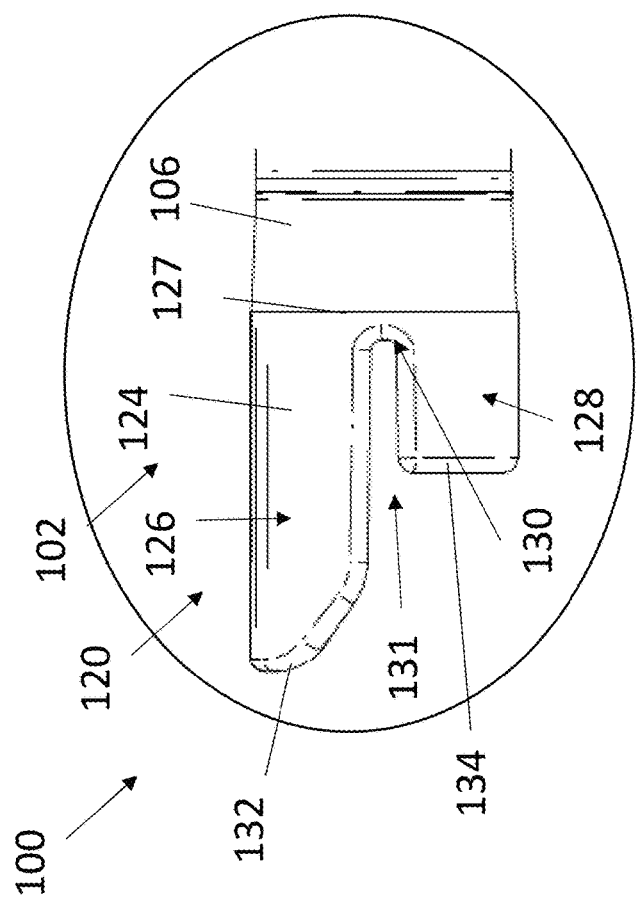
FIG. 5B is a close up view of a tip portion of the suction tool of FIG. 5
Figure 6:
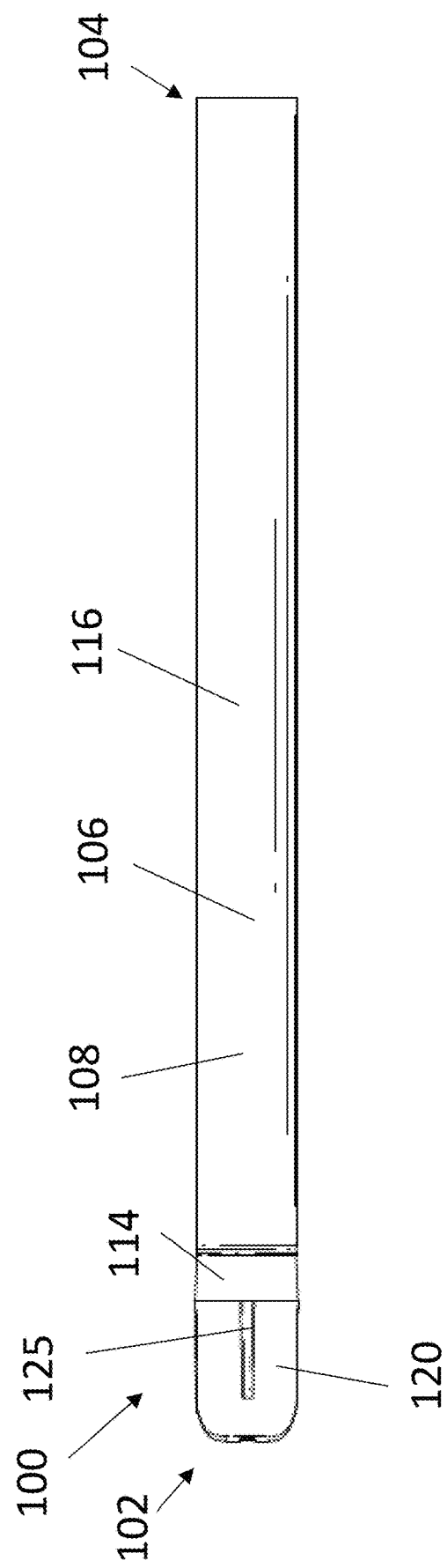
FIG. 6 is a top view of the suction tool of FIG. 1.

As mentioned, the suction tool 100 can include a tip portion 120. FIG. 5B illustrates a close-up view of the tip portion 120 as shown in FIG. 5A. The tip portion 120 can be positioned over at least a portion of the elongate body 106. For example, the tip portion 120 can be positioned over at least a portion of the suction end portion 102 of the suction tool 100. The tip portion 120 can be positioned over at least a portion of the outer surface 108. The tip portion 120 can be positioned over at least a portion of the inner surface 110. The tip portion 120 can include an internal surface 122 and an external surface 124, among other components. In some embodiments, at least a portion of the internal surface 122 can extend over at least a portion of the inner surface 110. In some embodiments, at least a portion of the external surface 124 can extend over at least a portion of the outer surface 108. The external surface 124 can include a slot 125 to reduce materials in the tip portion 120 and/or to simply manufacturing, among other benefits. In some embodiments, the external surface 124 and/or the internal surface 122 has a uniform thickness. In some embodiments, the external surface 124 and/or the internal surface 122 is tapered and/or has varying thicknesses.

In some embodiments, the internal surface 122 of the tip portion 120 can be larger than the external surface 124 such that the tip portion 120 extends further down the inner surface 110 of the elongate body 106 than the outer surface 108. The internal surface 122 can desirably protect matter that is received within a suction aperture 131 as described below, from the elongate body 106, which may be more rigid and/or hard. In some embodiments, the internal surface 122 and/or external surface 124 of the tip portion 120 can similarly or identically shaped and/or sized.

In some embodiments, the tip portion 120 can include a protective material, such as a coating, mold, or other material that is positioned over at least a portion of the elongate body 106. The protective material can be made of the same or different material from the elongate body 106. The tip portion 120 can be formed of any suitable material to provide protection to the mouth of the patient. For example, the tip portion 120 can be formed of a relatively soft material configured to protect a patient from the elongate body 106, which may be sharper and/or more rigid than the tip portion 120. The protective material can include, but is not limited to thermoplastic elastomers, rubbers, vulcanizates, and/or the like. In some embodiments, the tip portion 120 can include, for example, a cross-linked mixture of ethylene propylene diene monomer (EPDM) rubber and/or polypropylene, such as SANTOPRENE™ thermoplastic vulcanizate. The selection of the material of the tip portion 120 and/or the shape of the tip portion 120 can help to protect a patient's mouth from trauma caused by the suction tool 100.

In some embodiments, the wall thickness of the elongate body 106 at the tip portion 120 is less than the wall thickness of the elongate body 106 at the remainder of the elongate body 106. Such configurations can allow the external surface of the tip portion 120 to be approximately aligned with the remainder of the outer surface of the elongate body 106. Such configurations can allow the outer surface 108 to smoothly transition to the external surface 124. Such configurations can desirably reduce accidental traumas caused by the surface of the suction tool 100. Such configurations can desirably reduce the likelihood that the suction tool 100 will catch onto a portion of the patient's mouth in use.

Although the tip portion 120 is shown covering only a portion of the suction tool 100, the protective material can cover any amount of the suction tool, such as all or a portion of the suction tool 100 up to, for example 100% of the suction tool 100. In some aspects the entire elongate body 106, for example, can be made of and/or or coated with a suitable protective material, including the materials described herein. For example, from 5% to about 100% of the outer surface of the elongate body 106 may be made of, coated with and/or otherwise covered by a protective material.

The tip portion 120 can desirably provide additional support to the suction tool 100 at, for example, the suction end portion 102. The tip portion 120 can provide rigidity to the suction end portion 102.

The tip portion 120 can include an upper portion 126 and/or a lower portion 128. The upper portion 126 and the lower portion 128 can be integrally formed (e.g., formed as a single element). The upper portion 126 and the lower portion 128 can be connected by a recessed portion 130 to define a slot formed between the upper portion 126 and the lower portion 128. The recessed portion 130 (and the slot) may be formed between the upper portion 126 and the lower portion 128 on at least one or both sides of the tip portion 120. The slot can desirably reduce the pitch and/or level of noise produced by the suction tool 100 in use. The slot can desirably reach hard-to-reach areas of the patient's mouth. For example, the separation between the upper and lower portions 126, 128 can allow for easier access to certain portions of the patient's mouth to better evacuate matter. The slot may also help to reduce pressure build-up at a location distal of the connection between the tip portion and the elongate body. The slot may also help to reduce pressure build-up at a location on the tip portion as the airflow passes through the tip portion.

In some embodiments, the slot can define a release mechanism. For example, when the suction system is coupled to the suction tool 100 and the suction system is turned on, air is drawn through the suction tool 100. During a dental procedure, the tip portion of the suction tool 100 can become caught on a portion of the patient's mouth, such as the patient's cheek, for example. The slot can create a negative releasing pressure. The negative releasing pressure can help to limit or prevent the suction tool 100 from catching on a portion of the patient's mouth, such as the patient's cheek. The slot can desirably allow the suction tool 100 to safely disengage from the patient's cheek and/or pull away from the tissue of the patient's cheek without causing trauma.

The upper portion 126 and/or the lower portion 128 can be generally curved. For example, the upper portion 126 and/or the lower portion 128 can be shaped to form at least a portion of a circumference of a circle (see for example, FIG. 2). The circle can be concentric with the longitudinal axis of the elongate body 106. The shape formed by the upper portion 126 and/or the lower portion 128 can define a suction aperture 131 configured to receive matter therethrough. The suction aperture 131 can provide access to the central passageway 112 such that matter can pass through the tip portion 120 into the central passageway 112.

In some embodiments, the upper portion 126 can include an upper edge surface 132 and the lower portion 128 can include a lower edge surface 134. The upper and/or lower edge surfaces 132, 134 can be contoured. The upper and/or lower edge surfaces 132, 134 can be flat, curved, pointed, and/or the like. Such configurations can define a blunted and/or smooth surface. The upper and/or lower edge surfaces 132, 134 can be desirably shaped to minimize the sharpness of the tip portion 120. The upper and/or lower edge surfaces 132, 134 can be desirably shaped to reduce trauma caused to the patient's mouth and/or increase the comfort and safety to the patient.

In some embodiments, the upper portion 126 has an upper length that extends from a base 127 of the tip portion 120 to the upper edge surface 132 of the tip portion 120. The lower portion 128 can have a lower length that extends from the base 127 to the lower edge surface 131. The upper length can be greater than the lower length. Such configurations can allow for easier access to certain portions of the patient's mouth to better evacuate matter. Such configurations can help to reduce noise produced by the suction tool 100 in use. In some embodiments, the lower length is greater than or equal to the upper length.

In use, the suction tool 100 can be coupled with a suction system at the connection end portion 104 and the suction end portion 102 and/or tip portion 120 can be inserted into the patient's mouth to evacuate matter. After the dental procedure is over, the suction tool 100 can be decoupled from the suction system and discarded or sterilized for subsequent use.

As shown in at least FIGS. 2, 3, and 8, the suction tool can include a screen mechanism 150. The screen mechanism can be positioned within the central passageway 112. In some embodiments, the screen mechanism 150 is integrally formed with at least a portion of the suction tool 100, such as the elongate body 106. In some embodiments, the screen mechanism 150 can be formed as a separate component, for example. In such configurations, the screen mechanism 150 can be molded to the inner surface 110, press-fit within the central passageway 112, or otherwise coupled to the elongate body 106. The screen mechanism 150 can desirably block and/or catch certain matter that is larger than a certain size and/or can help to limit or prevent such matter from passing through the central passageway 112.

FIG. 2 illustrates a front view of an embodiment of the suction tool 100 and FIG. 3 illustrates a rear view of an embodiment of the suction tool 100. As shown, the screen mechanism 150 can be positioned within the suction tool 100. The screen mechanism 150 can act as a screen, filter, sieve, sifter, or sorter to prevent objects larger than a certain size from passing through the suction tool 100 to, for example, the attached suction system. As mentioned above, screening larger objects can prevent blockages within the suction tool 100 and/or suction system. Screening larger objects can help to prevent damage to the suction system caused by the evacuation of larger solid objects. The screen mechanism 150 and/or elongate body 106 can act to catch dental objects and/or restorations, such as custom dental implants and/or sterilized or other components, before the objects are evacuated through the suction tool 100 into the suction system.

The screen mechanism 150 can include one or more openings 152. The openings 152 can allow fluids, biologic and/or non-biologic materials, air, other gases, and/or objects smaller than a certain size to pass through the screening mechanism 150. The size and/or shape of the openings 152 can vary. In some embodiments, the openings 152 are identically sized and shaped. For example, the screening mechanism 150 can include a fine screen and/or mesh. The openings 152 can be of any suitable size to block and/or capture desired materials, while permitting sufficient suction and passage of materials such as saliva and blood, for example. In some embodiments, the openings 152 can be substantially polygonal.

The openings 152 can have a radius of approximately 0.06 centimeters. In some embodiments, the openings 152 can have a radius of approximately 0.02, 0.03, 0.04, 0.05, 0.06, 0.07, 0.08 centimeters or more. The openings 152 can have an area between approximately 0.5 and approximately 4.0 square millimeters. In some embodiments, the openings 152 are generally circular and have an area between approximately 2.0 and 2.5 square millimeters, and/or an area of approximately 2.0, 2.05, 2.1, 2.15, 2.2, 2.25, 2.3, 2.35, 2.4, 2.45, or 2.5 square millimeters, among other sizes. In some embodiments, the openings 152 are generally circular and have an area of approximately 2.25 square millimeters, for example. In some embodiments, the openings 150 are generally round with an area of between approximately 2.0 and 2.5 square millimeters. In some embodiments, the openings 152 are differently shaped. For example, a first opening 152 can be generally curvilinear and a second opening 152 can be generally polygonal. The openings can have an area that allows 40%, 50%, or 60% or more of the airflow to pass through the screen mechanism. In some implementations the openings occupy approximately 30%, 40%, 50%, 60%, or 70% or more of the area of the screen mechanism.

In some embodiments, the openings 152 are arranged to desirably reduce noise, reduce drag, increase suction pressure, and/or better allow smaller matter through the central passageway 112, among other benefits. The screen mechanism 150 can include a grate type configuration. Any suitable design can be used that can block or capture objects that are sucked into the suction tool 100, but which should not pass into the suction system. The size and/or shape of the openings 152 can be selected based in part on the dental procedure and/or the technical specifications of the suction system. For example, if the suction system the suction tool 100 connects to is not capable of evacuating objects having a cross-sectional area over a certain size, the openings 152 can be smaller than the certain size to inhibit damage to and/or prevent malfunction of the suction system. The size and shape of the openings 152 can be selected to maximize the efficiency of suction through the screen mechanism 150 and/or to reduce the noise produced by the suction tool 100 in use. For example, the size and shape of the openings 152 can maximize the negative pressure or suction through the screen mechanism 150 while simultaneously acting to filter, screen, or catch objects and/or reduce noise produced by the suction tool 100 in use.

As shown in at least FIGS. 2 and 3, the openings 152 can desirably have a circular shape. The screen mechanism can include nine openings 152. In some embodiments, the screen mechanism 150 can include one, two, three, four, five, six, seven, eight, nine, ten, eleven, or more openings 152. As mentioned above, the openings 152 (and the arrangement of the openings, such as the arrangement shown in FIGS. 2 and 3) can be arranged to maximize the negative pressure or suction through the screen mechanism 150 while filtering or catching matter and/or reducing the noise produced by the suction tool 100 in use. FIGS. 2 and 3 illustrate an embodiment of the screen mechanism 150 having an opening arrangement 154. The opening arrangement 154 can include a central opening 156 and one or more outer openings 158. In some implementations, as described herein, the opening arrangement 154 may include one or more circular openings 152. The one or more circular openings 152 may be arranged with a central opening surrounded by at least one outer opening. In some implementations, the opening arrangement 154 does not include a grid pattern (e.g., in which the openings are rectangles or squares and/or adjacent openings are spaced at right angles). In some implementations, as described herein, arrangements of the screen mechanism with circular openings (such as the arrangement described and shown herein) may reduce noise produced by the suction tool 100 in use by a greater amount than arrangements of the screen mechanism having the grid pattern.

The central opening 156 can be concentric with the elongate body 106. The central opening 156 can have a center that is aligned with the longitudinal axis of the suction tool 100.

The outer openings 158 can surround the central opening 156. The outer openings 158 can be uniformly spaced about the central opening 156. The outer openings 158 may additionally or alternatively be spaced (e.g., uniformly spaced) around the screen mechanism 150. For example, the outer openings 158 can be arranged in a circular shape that has a center aligned with the center of the central opening 156 and/or the elongate body 106. In some embodiments, the screen mechanism 150 includes eight or more outer openings 158. The openings 168 may be arranged to surround the central opening 156. In some embodiments, the screen mechanism 150 can include at least two or more outer openings 158. The two or more outer openings 158 can be equally spaced from the central opening 156 and/or positioned opposite one another about the central opening. For example, the two or more outer openings 158 can include a first outer opening 158A and a second outer opening 158B. The first outer opening 158A and the second outer opening 158B can be linearly arranged, such that the central opening 156 is positioned at a midpoint between the first outer opening 158A and the second outer opening 158B.

Figure 7:
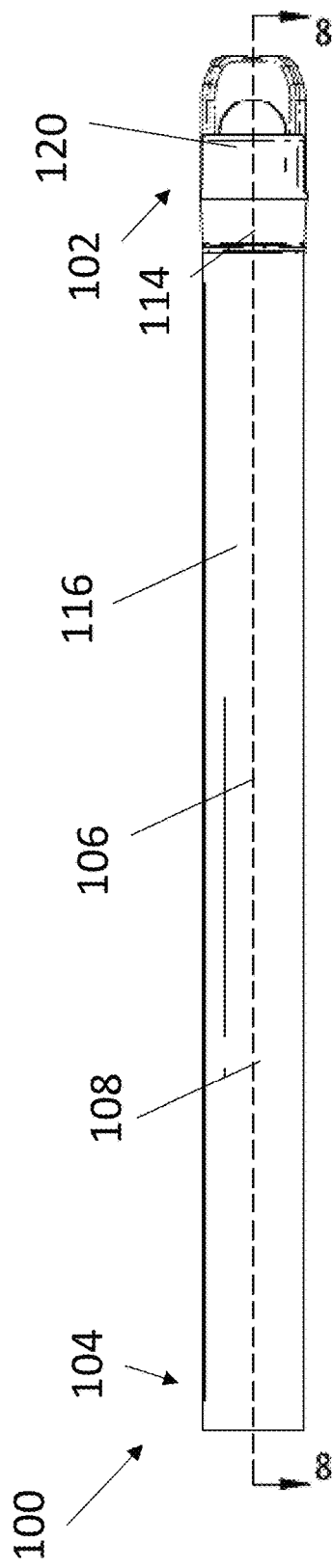
FIG. 7 is a bottom view of the suction tool of FIG. 1.

FIG. 8 illustrates a cross-sectional view of an embodiment of the suction tool 100 along the line 8-8 shown in FIG. 7. As discussed above, the screen mechanism 150 can be positioned within the passageway 112 between the suction end portion 102 and the connection end portion 104 of the suction tool 100. As shown in FIG. 8, the screen mechanism 150 can be desirably positioned within the central passageway at a distance from the proximal most end that is less than 80% of the total length 105 of the dental suction tool. As mentioned above, the total length 105 can extend from the proximal most end to the distal most end. The screen mechanism 150 can desirably be positioned within the central passageway at a distance from the distal most end that is less than 20% of the total length 105 of the suction tool 100. As described below, such configurations can desirably reduce the noise generated by the suction tool 100 in use. Such configurations can desirably provide a greater amount of volume for collecting dental materials. Such configurations can desirably provide better and/or more stable suction pressure.

In some embodiments, the screen mechanism 150 can be offset from the proximal most end of the suction end portion 102 by approximately 0.60 centimeters. In some embodiments, the screen mechanism is offset from the most proximal most end of the suction end portion 102 by approximately 0.50 centimeters to approximately 6 centimeters or any distance therebetween, for example. In some embodiments, the screen mechanism 150 can be offset from the most forward point on the suction end 110 by approximately 1.0 to approximately 3.0 centimeters. In some embodiments, the screen mechanism 150 can be offset from the most forward point on the suction end 110 by a distance that is between approximately 10% of the length of the suction tool 100. In some embodiments, the screen mechanism 150 is offset from the proximal most end by approximately 5% and approximately 95% of the length of the suction tool 100. In some embodiments, the screen mechanism 150 can be offset from the proximal most end on the suction end portion 102 by a distance that is between approximately 5% and approximately 25% of the entire length of the suction tool 100, for example, approximately 5%, approximately 6%, approximately 7%, approximately 8%, approximately 9%, approximately 10%, approximately 11%, approximately 12%, approximately 13%, approximately 14%, approximately 15%, approximately 16%, approximately 17%, approximately 18%, approximately 19%, approximately 20%, approximately 21%, approximately 22%, approximately 23%, approximately 24%, or approximately 25% of the entire length.

In some embodiments, the screen mechanism 150 can be offset from the suction end portion 102 to create the collection passageway portion 112C within the central passageway 112. For example, the collection passageway portion 112C can define the volume of space between the screen mechanism 150 and the suction end portion 102. The collection passageway portion 112C can receive and house objects or other matter that are evacuated through the suction end portion 102 of the suction tool 100 but cannot pass through the screen mechanism 150. In some embodiments, the screen mechanism 150 can prevent biologic and/or non-biologic materials including, but not limited to, cotton rolls, pieces of gauze, dental restorations, such as dental implants, dental implant components, and/or the like from passing therethrough. Dental implants, components of a dental implant, or dental restorations that are evacuated from a patient's mouth by the suction tool 100 can be received and/or stored within the collection passageway portion 112C until a dental professional removes the received component, implant, and/or restoration from the suction tool 100. The collection passageway portion 112C can act as a catch mechanism and prevent blockages of the suction tool 100 or attached suction system, damage to the suction system, and/or loss of sterilized dental objects. As mentioned above, the sterilized dental object can be very expensive. It can be desirable for the collection passageway portion 112C to catch the sterilized dental objects. The collection passageway portion 112C can desirably prevent dental objects from dropped into the patient's throat, and/or make it more difficult for the patient to inadvertently swallow a dental object.

Figure 9:
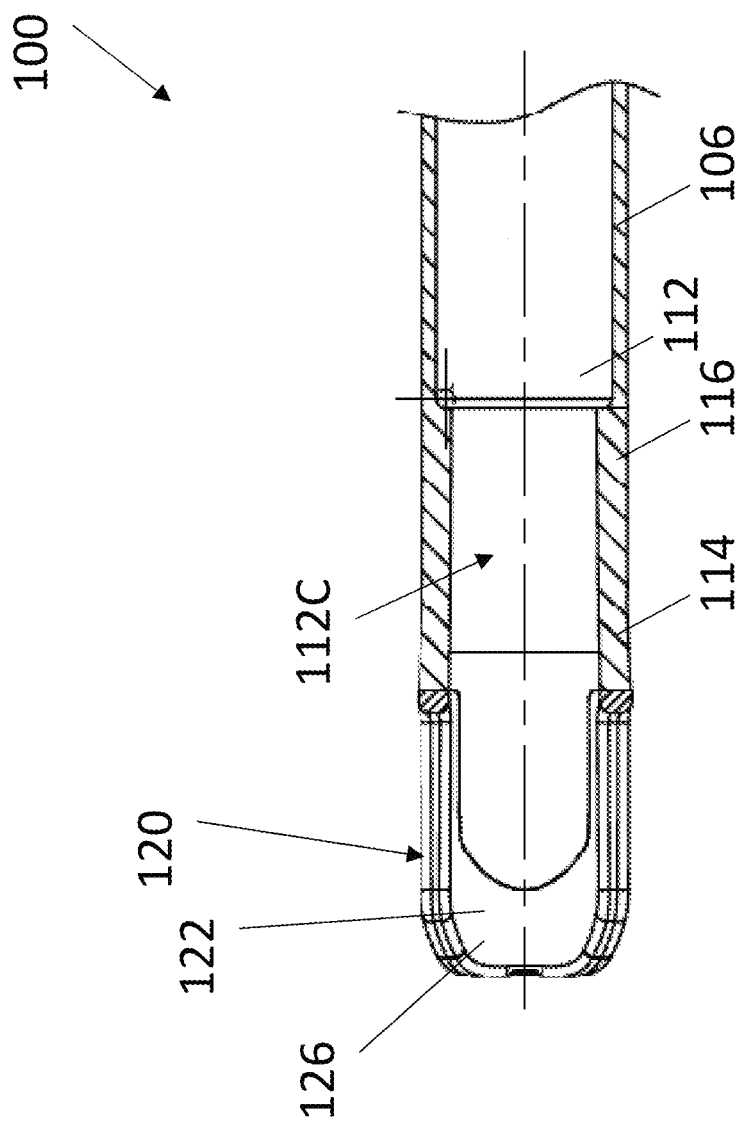
FIG. 9 is a side view of an embodiment of a portion of a suction tool.

FIG. 9 illustrates a side view of an example embodiment of at least a portion of the suction tool 100, such as the elongate body 106. The elongate body 106 can be generally tubular and includes the outer surface 108 and the inner surface 110. The inner surface 110 defines the central passageway 112 extending through the elongate body 106 between the connection end portion 104 and the suction end portion 102. The elongate body 106 can be formed using a variety of suitable methods, including for example, injection molding. In some embodiments, the elongate body 106 may include, for example, a rigid polypropylene.

The elongate body 106 can include a tip body portion 162 that can include a depressed or inset region 160 positioned near the suction end portion 102 in the outer surface 108. The tip body portion 160 and/or the depressed region 160 can have the same or similar shape to the tip portion discussed herein. The depressed region 160 can be used to define a space or area for molding, or otherwise attaching, a protective tip (not shown) to the elongate body 106. The elongate body can include one or more securement or engagement apertures disposed near the suction end portion 102 and extending through the outer surface 108 and/or inner surface 110. The securement apertures can be configured to receive a portion of the tip portion 120 (not shown) to secure the tip portion to the elongate body 106. In some embodiments, the tip portion 120 can be over-molded to the elongate body 106. In some embodiments, the liquid material that forms the tip portion 120 can seep through the securement apertures during the injection molding process such that the formed tip portion extends through the apertures in the elongate body 106. In some embodiments, the elongate body 106 can be released from a mold using a release agent, such as a silicone release agent. In some embodiments, other coupling arrangements can be implemented, such as interference fit, press fit, adhesive, and/or the like. In some embodiments, the elongate body 106 does not include a depressed region 160 and/or securement apertures. Similarly, some embodiments of HVE devices disclosed herein can be manufactured as a single unit.

Figure 10:
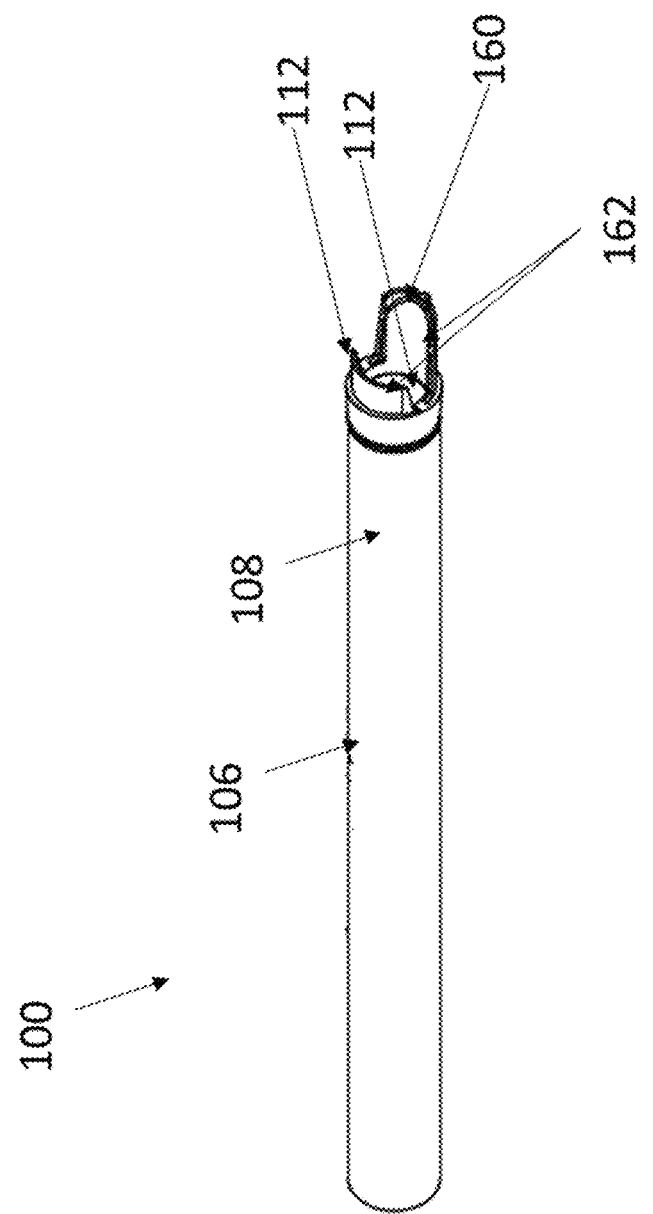
FIG. 10 is a partial side cross-sectional view of an embodiment of a suction tool.\

FIG. 10 illustrates a cross-sectional view of another embodiment of the suction tool 100. In some embodiments, the suction tool 100 shown in FIG. 10 can have the same or similar properties and/or components as the suction tool 100 described herein. In some embodiments, such as is shown in FIG. 10, the suction tool 100 may not include a screen mechanism 150.

As mentioned above, certain embodiments described herein can desirably reduce the level of noise exposure to dental professionals and/or patients. Such configurations can help to reduce hearing loss and/or other damage to the hearing of the dental professional and/or patient.

Several tests have been performed, which show a desirable decrease in the level of noise generated by suction through the embodiments of the suction tool described herein, in use. A test was performed on three variations of a suction tool connected to a suction system. The first device is the same or similar to the suction tool 100 shown in at least FIG. 1. For example, the first suction tool includes a screen mechanism having round openings, such as is shown in the pattern of at least FIGS. 2-3. The first device includes a unitary elongate body (e.g., without a side vent extending through a side portion of the elongate body). The first device includes a slot in the tip portion. The second device is the same or similar to the suction tool 100 shown in at least FIG. 10. The second device is similar to the first device, but does not include a screen mechanism, among other differences. The third device is similar to the first device and includes at least some of the same or similar features. For example, the third device includes an elongate body and a tip portion. The third device includes a screen mechanism having square openings in a grated or grid pattern. The grid pattern includes a plurality of rows of boxed-shaped openings equally spaced from one another. The elongate body of the third device includes a side vent extending through a side wall of the elongate body. The screen mechanism of the third device is positioned closer to the most distal point of the suction end portion of the tip portion than the side vent. The screen mechanism of the third device is positioned within the central passageway a distance from the most distal point of the suction end portion of the tip portion of the third device that is less than the distance at which the screen mechanism is positioned within the central passageway from the most distal point of the suction end portion of the tip portion of the first device. The fourth device is similar to the third device, but does not include a screen mechanism, among other differences. The background noise at the time the tests were performed was approximately 40 decibels (dB). Such background noise can be typical in a dental office or a patient's room. Table 1 below illustrates the test results for the first, second, and third devices.

TABLE 1

| Device | Average Noise (dB) | Minimum Noise (dB) | Maximum Noise (dB) | Length of Time (s) |
| --- | --- | --- | --- | --- |
| First Device | 70 | 68 | 74 | 10 |
| Second Device | 68 | 66 | 70 | 9 |
| Third Device | 95 | 94 | 98 | 8 |
| Fourth Device | 81 | 80 | 86 | 8 |

As shown in Table 1 above, the tests were performed for approximately 8-10 s for each device. The measurements were taken using a sound meter application after the suction system had been turned on. As shown in Table 1, the first device generated average, minimum, and maximum noise levels of 70 dB, 68 dB, and 74 dB, respectively. In some implementations, the suction tool described herein can produce maximum noise levels of 74 dB or less, 72 dB or less, 70 dB or less, 68 dB or less, 66 dB or less or lower levels. In some implementations, the screen mechanism described herein can produce maximum noise levels of 74 dB or less, 72 dB or less, 70 dB or less, 68 dB or less, 66 dB or less or lower levels. The third device generated the highest average, minimum, and maximum noise levels—95 dB, 94 dB, and 98 dB, respectively. The difference between the noise levels produced by the first and third devices can be significant. For example, the first device results in a noise reduction of approximately 20 dB to 30 dB. The average difference in measurements taken between the first device and the third device resulted in noise generation difference of approximately 25 dB. Such a reduction in noise generation can help to limit or prevent hearing loss or other damage to dental professionals and/or patients, as described herein. The second device, without the screen mechanism, generated noise levels lower than at least the fourth device, without the screen mechanism. For example, the second device generated average, minimum, and maximum noise levels of approximately 68 dB, 66 dB, and 70 dB, respectively. The fourth device generated average, minimum, and maximum noise levels of approximately 81 dB, 80 dB, and 86 dB, respectively. Compared to the fourth device, the second device resulted in a noise reduction of approximately 10 dB to 20 dB. The average difference in measurements taken between the second device and the fourth device resulted in noise generation difference of approximately 13 dB. Such configurations can desirably help to reduce or limit hearing loss or other damage caused to dental professionals and/or patients, as described herein.

The foregoing description details certain embodiments of the devices and methods disclosed herein. It will be appreciated, however, that no matter how detailed the foregoing appears in text, the devices and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

It will be appreciated by those skilled in the art that various modifications and changes may be made without departing from the scope of the described technology. Such modifications and changes are intended to fall within the scope of the embodiments, as defined by the appended claims. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A suction tool for connection to a dental suction system, the suction tool comprising:
    an elongate body comprising a first material, the elongate body including:
        a longitudinal axis extending between a suction end portion and a connection end portion that is configured to connect to the dental suction system;
        an inner surface defining a central passageway extending from the connection end portion to the suction end portion; and
        an outer surface;
    a tip portion extending over at least a portion of the elongate body and positioned at the suction end portion of the elongate body, the tip portion including:
        a second material;
        an upper portion; and
        a lower portion integrally formed with the upper portion and at least partially spaced apart from the upper portion by a recessed portion; and
    a screen mechanism positioned within the central passageway, the screen mechanism including a plurality of openings that are configured to allow evacuated matter to pass through;
    wherein the plurality of openings are circular, and the plurality of openings comprises a central opening concentrically aligned with the elongate body and a plurality of outer openings uniformly spaced and arranged in a shape that is concentrically aligned with the central opening.

2. The suction tool of claim 1, wherein an average noise level produced by the suction tool when the dental suction system is in operation is approximately 70 db or less.

3. The suction tool of claim 1, wherein the elongate body further includes:
an elongate region having a maximum diameter; and
a transition region positioned between the elongate region and the tip portion, the transition region having a maximum diameter that is greater than the maximum diameter of the elongate region.

4. The suction tool of claim 3, wherein the transition region is tapered between the elongate region and the tip portion.

5. The suction tool of claim 1, wherein a noise level produced by the suction tool when the dental suction system is in operation is approximately 74 db or less.

6. The suction tool of claim 1, wherein the elongate body has a wall thickness extending between the inner surface and the outer surface, and wherein the wall thickness defines a unitary body that extends from the connection end portion to at least the tip portion.

7. The suction tool of claim 1, wherein the screen mechanism is configured to reduce noise caused by suction through the dental suction tool.

8. The suction tool of claim 1, wherein the plurality of holes are not arranged in a grid pattern.

9. A method of reducing noise caused by suction through a dental suction tool, comprising:
providing a dental suction tool for use with a dental suction system, the dental suction tool comprising:
an elongate body including a first material and a central passageway extending from a connection end portion to a suction end portion, the elongate body defining a unitary body;
a tip portion extending over at least a portion of the elongate body and positioned at the suction end portion of the elongate body, the tip portion including:
a second material; and
a pressure prevention recess positioned between an upper portion and a lower portion of the tip portion; and
a screen mechanism positioned within the central passageway, the screen mechanism including a plurality of circular openings that are configured to allow evacuated matter to pass through, the plurality of circular openings comprising: a central opening concentrically aligned with the elongate body; and a plurality of outer openings uniformly spaced and arranged in a shape that is concentrically aligned with the central opening;
wherein at least the screen mechanism reduces noise caused by suction through the dental suction tool.

10. The method of claim 9, wherein the first material is the same as the second material.

11. The method of claim 9, wherein the first material is different from the second material.

12. The method of claim 9, wherein a noise level produced by the suction tool when the dental suction system is in operation is approximately 74 db or less.

13. The method of claim 9, wherein the plurality of holes are not arranged in a grid pattern.

14. A method of manufacturing a suction tool, comprising:
forming an elongate body defining a unitary body including:
a first material;
a longitudinal axis extending between a suction end portion and a connection end portion that is configured to connect to a dental suction system;
an inner surface defining a central passageway extending from the connection end portion to the suction end portion; and
an outer surface; and
a screen mechanism positioned within the central passageway, the screen mechanism including a plurality of openings that are configured to allow evacuated matter to pass through, wherein the plurality of openings are circular, and wherein the plurality of openings comprises a central opening concentrically aligned with the elongate body and a plurality of outer openings uniformly spaced and arranged in a shape that is concentrically aligned with the central opening; and
forming a tip portion extending over at least a portion of the elongate body and positioned at the suction end portion of the elongate body, the tip portion including:
a second material different from the first material;
an upper portion; and
a lower portion integrally formed with the upper portion and at least partially spaced apart from the upper portion by a recessed portion.

15. The method of claim 14, wherein a noise level produced by the suction tool when the dental suction system is in operation is approximately 74 db or less.

16. The method of claim 14, wherein the elongate body further includes:
an elongate region having a maximum diameter; and
a transition region positioned between the elongate region and the tip portion, the transition region having a maximum diameter that is greater than the maximum diameter of the elongate region.

17. The method of claim 16, wherein the transition region is tapered between the elongate region and the tip portion.

18. The method of claim 14, wherein the elongate body has a wall thickness extending between the inner surface and the outer surface, and wherein the wall thickness defines a unitary body that extends from the connection end portion to at least the tip portion.

19. The method of claim 14, wherein the screen mechanism is configured to reduce noise caused by suction through the suction tool.

20. The method of claim 14, wherein the plurality of holes are not arranged in a grid pattern.

* * * * *